United States Patent [19]
Mekalanos

[11] Patent Number: 4,882,278
[45] Date of Patent: Nov. 21, 1989

[54] NON-TOXINOGENIC VIBRIO CHOLERAE MUTANTS

[75] Inventor: John J. Mekalanos, Framingham, Mass.

[73] Assignee: President and Fellows of Harvard College, Cambridge, Mass.

[21] Appl. No.: 489,958

[22] Filed: Apr. 29, 1983
[51] Int. Cl.[4] ....................... C12N 15/00; C12N 1/20; C12R 1/63
[52] U.S. Cl. ............................. 435/172.3; 435/252.1; 435/252.3; 435/320; 435/909; 935/29; 935/56; 935/65; 935/72
[58] Field of Search ..................... 435/172.3, 253, 909, 435/317, 252.3, 252.1; 935/22, 23, 27, 29, 55, 56, 65, 72

[56] References Cited

FOREIGN PATENT DOCUMENTS

| | | | |
|---|---|---|---|
| 0018154 | 10/1980 | European Pat. Off. | 435/172.3 |
| 095452 | 11/1983 | European Pat. Off. | 435/172.3 |
| 2032955 | 5/1980 | United Kingdom | 435/172.3 |

OTHER PUBLICATIONS

Matzke et al., J. Molec. and Applied Genetics, vol. 1, pp. 39–49, 1981.
Chilton et al., Stadler Symposium, vol. 13, pp. 39–52, 1981.
Sublett R. et al., *Inf. & Immun.*, vol. 32, pp. 1132–1138, 1981.
Sutcliffe et al., Genetic Engineering (Chakrabarty ed), pp. 83–100, 1978.
Thomson J. et al., *J. Bact.*, vol. 148, pp. 374–378, 1984.
Kaper J. et al., *Inf. & Imm.*, vol. 32, pp. 661–667, 1981.
Honda T. et al., *Proc. Natl. Acad. Sci.*, vol. 76, pp. 2052–2056, 1979.
Sigel S. et al., *Infection & Immunity*, pp. 474–479, May 1981.
Mekalanos J. et al., *Nature*, vol. 306, pp. 551–557, Dec. 1983.
Mekalanos J., *Cell*, vol. 35, pp. 253–263, Nov. 1983.
Holme et al., Acute Enteric Infections in Children, New Prospects for Treatment and Prevention (1981) Elsevier/North-Holland Biomedical Press, Ch. 26, pp. 443 et seq. (Levine et al.).
Cash et al., (1974), J. Infect. Dis. 129: 45–52.
Pearson and Mekalanos (1982), Proc. Natl. Sci. USA 79: 2976–2980.
Gill (1975), *Proc. Nat'l. Acad. Sci.*, USA 72: 2064–2068.
Cuatrecasas, *Biochem.* 12: 3577–3581 (1973).
Finklestein et al., (1974), *J. Infect. Dis.*, 129: 117–123.
Mekalanos et al., (1982), *Proc. Nat'l. Acad. Sci.*, USA 79: 151–155.
Woodward et al., (1975), *Proc. 11th Jt. Conf. on Cholera NIH*, p. 330.
Lai et al., (1979), Abstracts of the 11th International Congress of Biochemistry, Toronto, Canada, p. 207, Abstract 03–45173.
Ruvken et al., (1981), Nature (London), 289: 85–88.
Beringer et al., (1978), Nature, 276: 633–634.
Kaŝper and Levine, Lancet, Nov. 21, 1981, pp. 1162–1163.
Gennaro et al., Nucleic Acids Research, 10(16): pp. 4883–4890 (1982).
Guerrant et al., (1974), Infect. Imm. 10: 320–327.
Southern (1975), J. Molec. Biol. 98: 503–517.
Dallas (1979), J. Bact. 139: 850–858.

*Primary Examiner*—Jayme A. Huleatt

[57] ABSTRACT

A genetically stable nontoxinogenic form of the Ogawa 395 strain of *Vibrio cholerae* which has a deletion mutation in both copies of the $A_1$-peptide-encoding gene, resulting in the loss of a gene sequence required for expression of a toxic $A_1$ peptide is disclosed, as well as plasmids and methods for making the strain. The strain is useful as a live or dead oral vaccine.

13 Claims, 3 Drawing Sheets

FIG. 2B 0395-N1 Construction

FIG. 3

NON-TOXINOGENIC VIBRIO CHOLERAE MUTANTS

BACKGROUND OF THE INVENTION

This invention relates to modified strains of *Vibrio cholerae* that are useful, for example, for immunological protection against cholera and other diseases, as well as to plasmids and methods used to make those strains.

Cholera is a diarrheal disease caused by *Vibrio cholerae*, a gram-negative bacterium. Orally ingested, *V. cholerae* grows in the upper intestine of man and produces a soluble protein, cholera toxin, which is responsible for the diarrhea observed in the disease. The toxin is composed of two types of subunits, A and B, and the activity of the intact toxin finds its origin in a proteolytic fragment of the A subunit, the $A_1$ peptide, which is an enzyme that activates the adenylate cyclase system of target cells [Gill (1975) Proc.Nat'l.Acad.Sci. U.S.A. 72: 2064–2068]. The resultant increase in cyclic AMP in intestinal cells causes the diarrhea seen in the disease. The B subunit is nontoxic, although it does bind to the target cell and facilitate the transport of the $A_1$ peptide through the cell's membrane [Cuatrecasas, Biochem. 12: 3577–3581 (1973)]. Antibodies directed at the B subunit efficiently inactivate the toxin by blocking the binding of the toxin to the cell surface [Id].

Because cholera toxin is an intestinal disease, commercially available killed bacterial and toxoid vaccines have been relatively ineffective in inducing immunity when administered parenterally. Since the disease itself induces immunity, one must conclude that local intestinal immunity mediated by secretory IgA is probably the most important aspect of acquired immunity to cholera. To stimulate local immunity in the intestine, the bacterial antigens must be delivered through the acid and proteolytic barrier of the stomach. For this reason, live, oral cholera vaccines have been proposed.

Mutants of *V. cholerae* have been isolated which produce no toxin or produce only the B subunit of the toxin [Finklestein et al., (1974) J. Infect. Dis. 129: 117–123; Honda et al., (1979) Proc.Nat'l.Acad.Sci. USA 76: 2052–2056; Mekalanos et al., (1982) Proc.Nat'l.Acad.-Sci. USA 79: 151–155]. However, to be an optimum candidate for a live anti-cholera vaccine, a mutant should: 1) be well-characterized and genetically stable (i.e., it should not revert to the toxin-producing wild-type); 2) colonize well in the intestine; and 3) provide long-lived, broad-based immunity. Mutants produced thus far, for example, those produced by chemical mutagenesis or those produced from parent strains not known to have optimal colonization and immunity-producing ability, may pose problems in one of the three areas listed above, even though preliminary testing in human volunteers shows they are relatively innocuous and they induce significant immunity [Woodward et al. (1975), Proc. 11th Jt. Conf. on Cholera NIH, p. 330; Holme et al., *Acute Enteric Infections in Children, New Prospects for Treatment and Prevention* (1981) Elsevier/-North-Holland Biomedical Press, Ch. 26, pp. 443 et seq. (Levine et al.)]

SUMMARY OF THE INVENTION

The invention features, in one aspect, a genetically stable, nontoxinogenic form of the Ogawa 395 strain of *Vibrio cholerae* which has a deletion mutation in both copies of the $A_1$-peptide-encoding gene (ctx A) resulting in the loss of a gene sequence required for expression of a toxic $A_1$ peptide.

In preferred embodiments, each copy of the ctx A gene sequence is missing at least the portion of the gene sequence which codes for amino acids 41 through 101 (and most preferably, for amino acids 10 through 164) of the $A_1$ subunit; either the ctx B gene sequence is intact, or the deletion mutation includes a portion of the B-subunit encoding gene required for expression of an effective B-subunit; and the *V. cholerae* has the identifying characteristics of ATCC Deposit Nos. 39,346 or 39,347.

In other aspects, the invention features a method of making a genetically stable form of *V. cholerae* that is incapable of expressing a toxic $A_1$ peptide, and a plasmid used in that method.

In preferred embodiments, the method includes the steps of isolating a first plasmid containing the ctx A and ctx B genes and DNA segments bracketing both sides of those genes; constructing a second plasmid from the first plasmid, in which a sequence in the $A_1$-peptide-encoding gene required for expression of a toxinogenic $A_1$ peptide is deleted; recombining a segment of the second plasmid which includes the bracketing gene segments onto the chromosome of a *V. cholerae* strain known to colonize the intestine and to be immunogenic, thus replacing one copy of the ctx A gene on the chromosome with the deletion mutation; and growing the resulting microorganism for several generations to allow spontaneous transfer of the mutation onto the other copy of the ctx A gene. Also in preferred embodiments of the method, the second plasmid includes a genetic marker to verify the recombination step, the strain used for the recombination step is Ogawa 395, and the deletion involved is as described above.

The plasmid comprises a DNA sequence corresponding to the segment of the chromosome which brackets the ctx A-ctx B gene of a strain of *V. cholerae*, and the plasmid lacks at least a segment of the ctx A gene required for expressing a toxic $A_1$ peptide.

Other features and advantages of the invention are apparent from the following description of the preferred embodiments and the claims.

DESCRIPTION OF THE PREFERRED EMBODIMENTS

I first briefly describe the drawings of the preferred embodiments.

Figure 1:
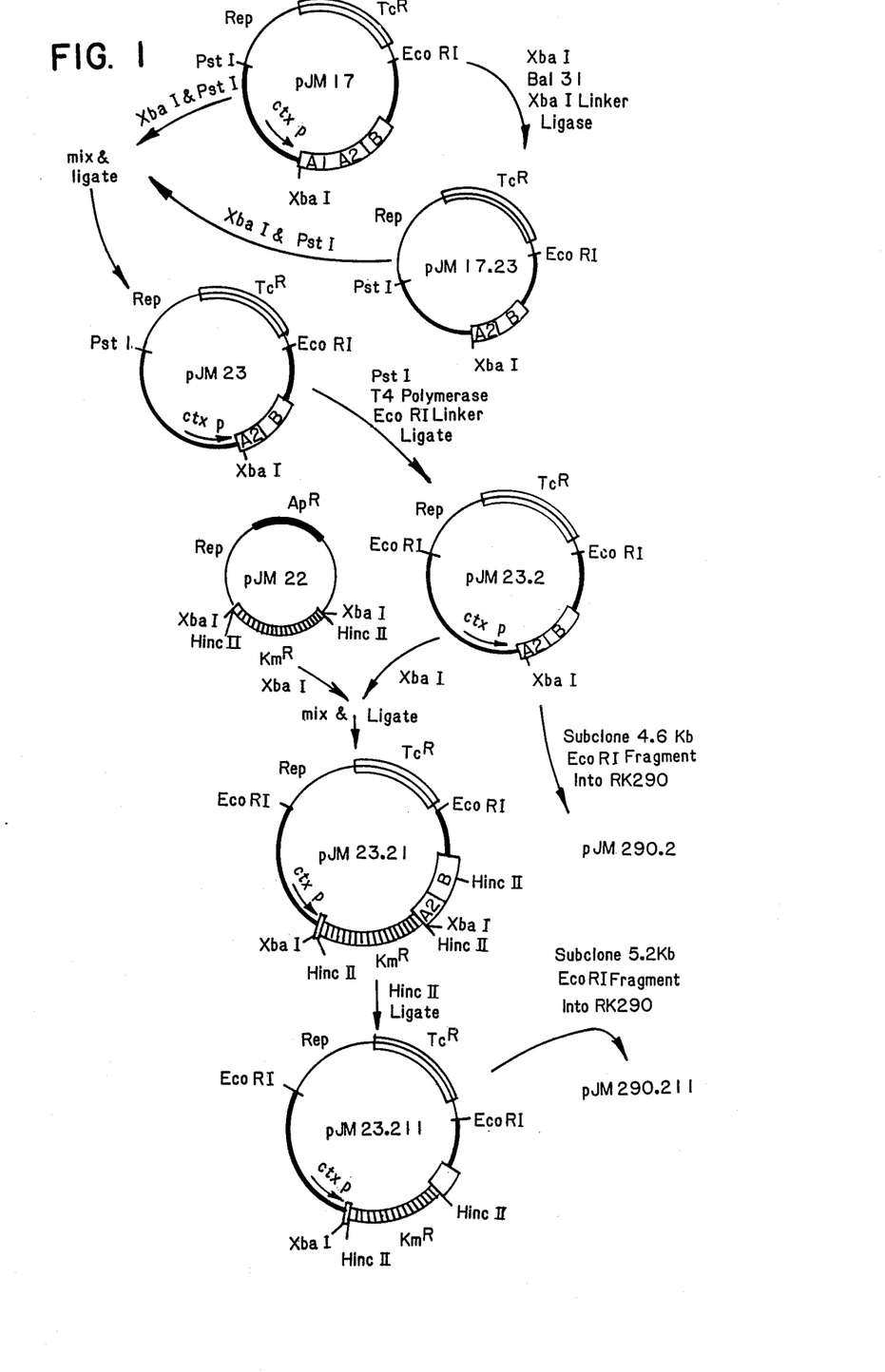
FIG. 1 is a diagram representing the steps of the method of creating a plasmid to be recombined onto the chromosome of *V. cholerae*.
Figure 2A:
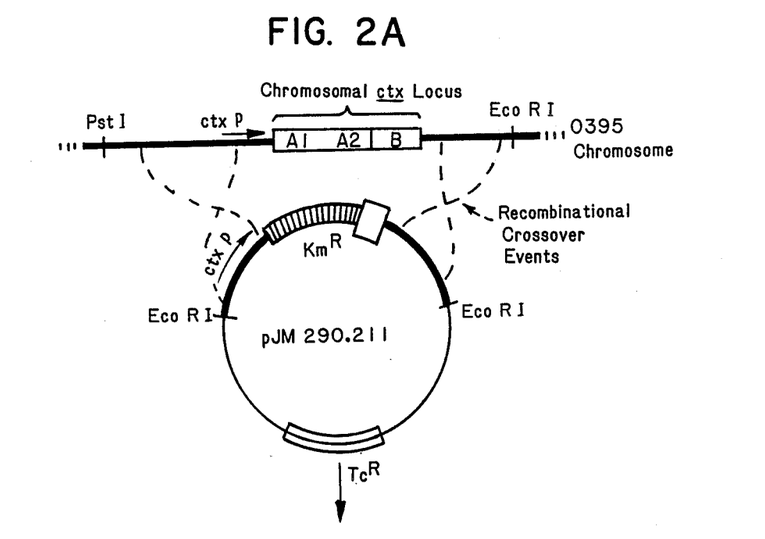
FIGS. 2A and B are diagrams representing the steps for recombination of plasmids from FIG. 1 onto the chromosome of *V. cholerae*.
Figure 2B:
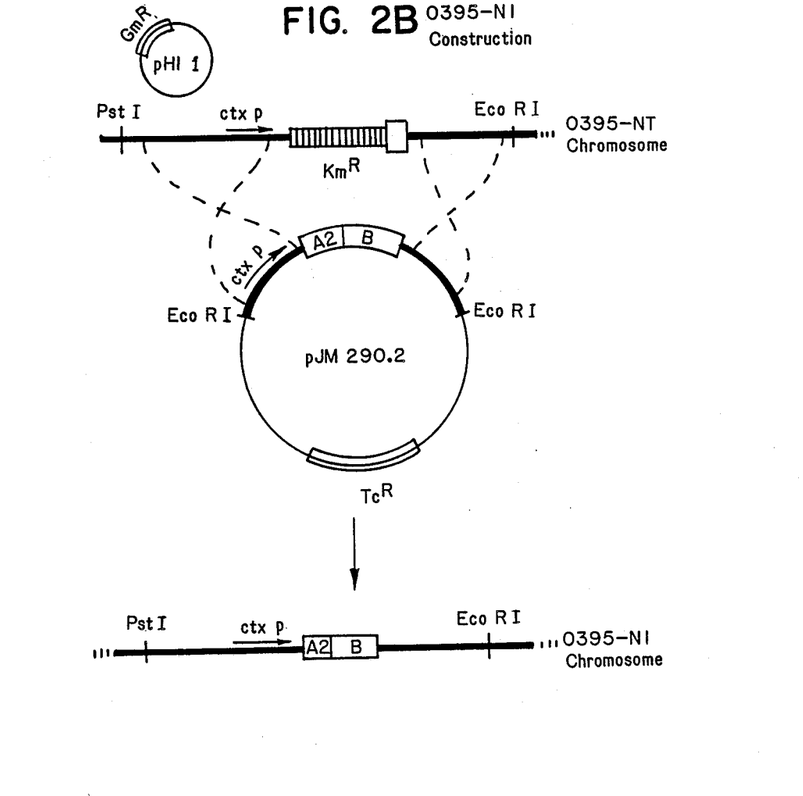

The following abbreviations apply to FIGS. 1 and 2.

| Gene Sequence | Resistance Markers |
|---|---|
| ctxp = toxin promoter | Gm = gentomycin |
| $A_1$ = $A_1$ subunit sequence | Tc = tetracycline |
| $A_2$ = $A_2$ subunit sequence | Km = kanamycin |
| B = B sequence | Rep = origin of plasmid replication |

Conditions used for digestion of the plasmids with the indicated restriction enzymes were those suggested by the vendor, New England Biolabs, Beverly, Mass. Similarly, T4 DNA polymerase, Nuclease Bal-31, Klenow fragment, and DNA ligase were used as suggested by their manufacturer, Bethesda Research Labs, Inc., Bethesda, Md. Xba I and Eco R1 linkers were purchased from New England Biolabs. The open boxes labeled A1, A2, and B represent the corresponding regions of the ctxA and ctxB genes. The heavy lines show *V. cholerae* DNA which is adjacent to the toxin genes.

I. Selecting the Parental Strain

The parental strain of *V. cholerae* used to construct a mutant for live vaccines should induce long-lasting, comprehensive protection and should colonize well in the human intestine. Ogawa 395 has demonstrated an ability to induce an immunity lasting three years which is generally effective against infection by other strains. It also colonizes well in the intestine.

II. Constructing the Plasmid

In broad outline, a plasmid (pJM17) prepared from DNA of wild-type Inaba 569B *V. cholerae* according to the procedure of Pearson and Mekalanos (1982) Proc. Natl. Sci. USA 79: 2976–2980, contains genes for the A toxin subunit (ctx A) and the B toxin subunit (ctx B), as well as for tetracycline resistance ($Tc^R$).

As shown in FIG. 1, the pJM17 plasmid was linearized with XbaI and then exonucleolytically digested with Bal31. Since the XbaI site resides within the ctxA gene, this procedure resulted in deletion of ctxA sequences. Ligation of the Bal-31 digests in the presence of an XbaI DNA linker resulted in the construction and isolation of plasmid pJM17.23. Reassortment of the PstI-XbaI fragments of pJM17 and pJM17.23 resulted in construction of pJM23. This plasmid contains an internal 450 base pair deletion in ctxA. The position of this deletion within the ctxA gene was confirmed by DNA sequencing which showed that over 80% of the sequence required for production of the $A_1$ peptide was deleted. Specifically, the ctxA deletion carried by pJM23 removes the DNA encoding amino acid residues 10 through 164. Since the enzymatically active $A_1$ peptide is 192 amino acid residues in length, this deletion removes over 80% of the required information for $A_1$. The DNA sequence of the ctxA deletion is shown below:

AGT AAC TTA GAT ATT GCT CCA GCA GCA GAT GGT TAT GGA TTG GCA GGT TTC CCT CCG GAG CAT AGA GGT TGG
SER ASN LEU ASP ASP ILE ALA PRO ALA ALA ASP GLY TYR GLY LEU ALA GLY PHE PRO PRO GLU HIS ARG ALA TRP
       155                              160                    165                    170 continues to residue #10

It has been reported that a 12,500 dalton molecular weight fragment of $A_1$ peptide, which contains the region from MET-41 to MET-101, retains 35% of the enzymatic activity of a complete $A_1$ peptide [Lai et al.(1979) Abstracts of the 11th International Congress of Biochemistry, Toronto, Canada, p. 207, Abstract 03-4s173]. The active site of the $A_1$ peptide thus lies on that 12,500-dalton fragment, and, even if it is not within the 6600-dalton region between MET-41 and MET-101, it cannot lie more than about 54 amino acids (5900 daltons) past the MET-101. The active site is thus well within the ctxA deletion of plasmid pJM 23. Deletion of the amino acids between amino acid 41 and 101 (or most preferably, to ensure total absence of toxinogenicity, between amino acids 10 and 164) assures lack of $A_1$ toxinogenic activity.

Plasmid pJM23 is shown to code for production of B subunit in both *E. coli* and in *V. cholerae,* thus showing that deletion mutations in ctxA have little effect on expression of ctxB. The following results (Table 1) were obtained by assaying total B subunit produced in 18 Hr CYE cultures by enzyme linked immunosorbant assay. Less than 0.005 μg/ml of B subunit could not be detected. ND means not determined because the experiment was prohibited.

TABLE 1

B subunit Production by Recombinant Plasmids

| Plasmid | *In E. coli* MS371 | In *V. cholevae* M7922 |
|---|---|---|
| pJM17 | 0.3 μg/ml | ND |
| pJM23 | 0.2 μg/ml | 9.0 μg/ul |
| pJM290.2 | 0.05 μg/ml | 1.5 μg/ul |
| pJM23.211 | 0.005 μg/ml | 0.005 μg/ml |
| pJM290.211 | 0.005 μg/ml | 0.005 μg/ml |

III. Recombination Onto the Chromosome

Referring again to FIG. 1, two plasmids, pJM23.2 and pJM23.211, are constructed from pJM 23. Fragments of those plasmids are then cloned onto another plasmid (RK290) [Ruvken et al. (1981) Nature (London) 289:85-88] for use in marker exchanges depicted in FIG. 2 and described below.

A. Strain 0395-N1; from Plasmid pJM23

As shown in FIG. 1, pJM 23 is converted to a derivative plasmid pJM 23.2 by digestion with Pst I and $T_4$ polymerase followed by ligation in the presence of Eco RI linker. pJM 23.2 is identical to pJM23, except that the Pst I site has been replaced by a Eco RI site. From pJM 23.2 a plasmid (pJM 23.211) is constructed with a DNA fragment encoding for resistance to kanamycin ($Km^R$) inserted approximately at the junction of the ctxA to ctxB deletion originally on pJM23.

This is accomplished by digesting pJM 23.2 with XbaI in the presence of the XbaI products of plasmid pJM22 carrying $Km^R$ flanked by XbaI/Hinc II sites. The resulting plasmid pJM 23.21 is digested with Hinc II and ligated to create pJM 23.211, which has a ctx A deletion starting at amino acid 10 and extending through ctx B to the Hinc II site.

The $Km^R$ gene provides a selective marker with which to obtain the recombinants of 0395 which have replaced both their resident ctxA genes with the deletion mutation carried by pJM23.211.

A marker exchange procedure is then used to effect recombination onto the chromosome, as follows: A spontaneous streptomycin resistant ($Sm^R$) derivative of 0395 is first made by plating out about $10^{10}$ Ogawa 0395 cells on medium containing 100 μg/ml of streptomycin. This derivative is used in all subsequent experiments.

Plasmid pJM290.211 is transferred to 0395 $Sm^R$ by conjugation using plasmid RK2013 [Ruvkin et al. (1981) Nature (London) 289: 85-88] as a mobilizer. 0395 $Sm^R$ cells carrying pJM290.211are $Sm^RTc^RKm^R$. These are superinfected with another plasmid pHI1 [pHI1 is the same as plasmid. pHI1J1, reported by Beringer et al. (1978) Nature 276:633-634], which is $Gm^R$, and $Gm^RKm^R$ colonies are selected. pHI1 and pJM290.211 cannot stably coexist in the same cell because of an incompatibility barrier. Thus, in order for the cell to remain $Km^R$, must recombine the DNA coding for this resistance onto the 0395 chromosome.

FIG. 2A shows the crossover events between a chromosomal copy of the ctx genes and the deletion derivative carried by plasmid pJM290.211. The appropriate recombinants were recovered by superinfecting with incompatible plasmid pH11 and selecting $Gm^RKm^R$. The structure of such a recombinant, 0395-NT, is shown. The site on the 0395 chromosome where the $Km^R$ will end up is determined by the DNA sequences flanking the $Km^R$ fragment. Since the flanking sequences are derived from DNA which flanks the toxin genes on the chromosome, the result shown in FIG. 2A occurs, and the resident genes are replaced by the mutant genes carrying the $Km^R$ insert. The extent of the DNA on pJM 23.211 which brackets the ctx A and ctx B gene sites and corresponds to the wild-type chromosomal DNA sequence can be expressed as the distance between the Eco RI site and the Xba I site in the A gene fragment on pJM 23.21 (2.7 kilobases) and the distance between the Hinc II site in the B gene, and the Eco RI site adjacent the $Tc^R$ gene (1.4 kilobases). Thus, the deletion mutation is recombined onto the chromosome and replaces one normal copy of the ctx locus.

Since 0395 has two copies of the toxin locus, it is necessary to recombine the 290.211 deletion mutation into both of these. Surprisingly, this is simply accomplished by growing strains carrying one marker exchanged copy for several generations during which time recombination events resulted in the spontaneous transfer of the mutation into the other copy. 0395 derivatives carrying the deletion mutations in both copies are then recognized by colony hybridization using a probe (the 0.95Kb XbaI/Hinc II fragment of pJM17) which specifically hybridizes to the DNA absent in the deletion mutation. Colonies unreactive with this probe are then checked by Southern hybridization to confirm the loss of the sequence removed by the deletion. The migration of the bands confirms that the expected size deletions of the A gene are introduced into each of the two resident ctx gene copies of 0395 to give strain 0395-NT.

As expected for a ctxA-ctxB deletion, Strain 0395-NT produces neither the A nor the B subunit since portions of both these genes were deleted on pJM290.211. The results below (table 2) show total B subunit antigen produced in 18 Hr CYE cultures and assayed by enzyme linked immunosorbant assay. Less than 0.005 μg/ml of B subunit could not be detected. Total toxin activity expressed in terms of μg/ml of purified cholera toxin. The same culture supernatant fluid was assayed as above for B subunit. The toxicity assay was the CHO-cell assay performed as described by Guerrant et al. (1974) Infect. Imm. 10: 320-327.

TABLE 2
B Subunit and Toxin Activity Produced by *V. cholerae* Derivatives

| Strain | B Subunit Antigen | Toxin Activity |
| --- | --- | --- |
| 0395 | 0.3 μg/ml | 0.3 μg/ml |
| 0395-NT | 0.005 μg/ml | 0.001 μg/ml |
| 0395-N1 | 0.3 μg/ml | 0.001 μg/ml |

B. Strain 0395-N1

The construction present on pJM23.2 is crossed onto the chromosome by a modified marker exchange procedure. Plasmid pJM290.2 is formed by transferring a 4.6 kilobase pair fragment from pJM 23.2 onto RK290. Plasmid pJM290.2 is then transferred into strain 0395-NT which has each of its two ctx copies tagged with a $Km^R$. Introduction of pJM290.2 into this strain then allowed crossover events to subsequently replace the $Km^R$-tagged copies with the construction on pJM290.2. These recombinant colonies were recognized by their sensitivity to Km.

Figure 3:
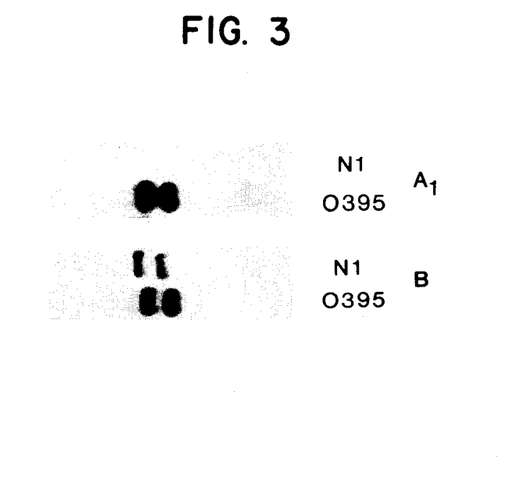
FIG. 3 is a copy of a photograph of a Southern blot analysis.

Specifically, as shown in FIG. 2B strain 0395-NT was cured of pHI1 and then pJM290.2 was transferred into the strain. After about 50 generations of growth, spontaneous $Km^s$ recombinants were isolated by replica plating. One of these was cured of pJM290.2 and has the structure shown (0395-N1). Southern hybridization to confirm the structure of one of these to give strain 0395-N1 is done as follows:

DNA is prepared from strain 0395 and 0395-N1. The DNA is digested with XbaI and analyzed by the method of Southern. (1975) J.Molec.Biol.98: 503–517 with either an $A_1$ probe (the 580 base pair XbaI-Hind III fragment of 5 EWD299 [Dallas (1979) J.Bact.139: 850–858], or B probe (the 590 base pair EcoRI-Hind III fragment of EWD299). The two ctx loci of 0395 are seen as two bands which react with both probes. Strain 0395-N1, however, reacts only with the B probe, and the bands which do react are smaller in size by the ctxA deletion originally present on pJM23. FIG. 3 is a copy of a photograph of blots from such a Southern hybridization showing that 0395-N1 has lost the sequence homologous to a probe derived from the $A_1$ region, but retains the sequence for the B subunit, which reside on a restriction fragments that are smaller by the size of the ctx $A_1$ deletion on plasmid pJM 23 (450 base pairs). Consistent with this result, 0395-N1 produced normal amounts of the B subunit when compared to the 0395 parental strain, but displayed no toxicity in CHO cells (Table 2, above). Thus, 0395-N1 is identical to the parental strain 0395 except for the ctxA deletion originally present on pJM23.

The resulting strains and plasmids have been deposited with the American Type Culture Collection and have the following deposit numbers:

| Strain 0395-N1 | 39,346 |
| --- | --- |
| Strain 0395-NT | 39,347 |
| Plasmid pJM 290.2 | 39,348 |
| Plasmid pJM 290.211 | 39,349 |

The ATCC deposit samples will be freely available upon issuance of a United States patent hereon, upon publication of a European or Japanese application hereon, or in accordance with the laws of any country in which a patent application is filed.

IV. Use

Both strain 0395-N1 and strain 0395-Nt are useful as sources of immunologial protection against cholera infection. They are useful for both live and dead vaccines.

Strain 0395-N1 is produced from a background strain that is known to colonize well in the intestine and to provoke a strong immunity reaction. The mutant strain has been demonstrated to be genetically altered only insofar as it has a deletion mutation which prevents the expression of a toxinogenic $A_1$ toxin subunit. The strain is useful, inter alia, as a vaccine prepared and administered under the dosages and conditions described in Holme et al., *Acute Enteric Infections in Children, New Prospects for Treatment and Prevention* (1981) Elsevier/-North-Holland Biomedical Press, Ch. 26, pp. 443 et seq. (Levine et al.).

The fact that individuals infected with toxinogenic *V. cholera* Ogawa 395 do not excrete significant quantities of intact cells indicates that a cell-targeted immunological defense in addition to anti-toxin defenses are involved. Strain 0395-NT, while lacking genetic information to produce the B-subunit of the toxin, nevertheless possesses other immunogenic traits of the Ogawa 395, and is useful as a vaccine prepared and administered as described above.

The plasmids and methods described are useful for making 0395-NT and 0395-N1 strains and may also be used for making strains which express the B subunit with some other antigen. Such strains could then be used in a vaccine to take advantage of the improved immunogenicity realized by attaching an antigen to the B-subunit and thus using the B-subunit as a cell recognition and attachment vehicle.

What is claimed is:

1. A nontoxinogenic genetically stable strain of *Vibrio cholerae* Ogawa 395 which is derived from a parent *V. cholerae* organism comprising at least two copies of a ctxA gene encoding a toxic $A_1$ peptide, said strain having a genetically engineered deletion mutation resulting in loss of at least a part of each copy of said ctxA gene required for expression of a toxic $A_1$ peptide.

2. The strain of claim 1 further characterized in that said strain lacks at least that portion of each copy of said ctxA genes of said parent *V. cholerae* organism which code for amino acid residues 10–164.

3. The strain of claim 1 further characterized in that said strain lacks at least 80% of the sequence of each copy of said ctxA gene of said parent *V. cholerae* organism.

4. The strain of claim 1 further characterized in that said strain comprises a ctxB gene encoding a B subunit peptide.

5. The strain of claim 1 further characterized in that said strain comprises the genome of said parent *V. cholerae* organism, intact, except for said deletion mutation.

6. The strain of claim 1 wherein said parent *V. cholerae* organism comprises a ctxB gene encoding a B subunit peptide, and said deletion mutation includes at least a portion of said ctxB gene required for expression of a complete B subunit peptide, and said deletion mutation includes at least a portion of said ctxB gene required for expression of a complete β subunit.

7. A bacterial strain having all of the identifying characteristics of either ATCC Deposit No. 39346 or ATCC Deposit No. 39347.

8. A method of producing a genetically stable strain of *Vibrio cholerae* Ogawa 395 that is incapable of expressing a toxic $A_1$ peptide, comprising, providing a wild-type strain of *Vibrio cholerae* Ogawa 395 which has at least two copies of a ctxA gene on its chromosome and which is known to colonize in the intestine and to be immunogenic;

genetically engineering a deletion mutation in one copy of said ctxA gene so as to delete a DNA sequence required for expression of a toxic $A_1$ peptide; and growing the resulting altered *V. cholerae* for several generations to allow spontaneous transfer of the deletion mutation to said second copy of said ctxA gene.

9. A method of producing a genetically stable strain of *Vibrio cholerae* Ogawa 395 that is incapable of expressing a toxic $A_1$ peptide, comprising, providing a first plasmid which contains *V. cholerae* DNA comprising a ctxA gene, a ctxB gene and DNA segments bracketing both sides of said ctxA gene and said ctxB gene;

constructing a second plasmid from the first plasmid, the second plasmid being altered in that at least a segment of said ctxA gene required for expression of a toxic $A_1$ peptide has been deleted; and recombining a segment of the second plasmid, which includes said bracketing DNA segments, onto the chromosome of a parent *V. cholerae* Ogawa 395 organism which has at least two copies of a ctxA gene on its chromosome and which is known to colonize in the intestine and to be immunogenic, thus replacing one copy of said ctxA gene on said parent *V. cholerae Ogawa* 395 chromosome;

and growing the resulting altered *V. cholerae* for several generations to allow spontaneous transfer of the deletion mutation to said second copy of said ctx A gene.

10. The method of claim 9 wherein said second plasmid includes a marker to verify said recombination step.

11. The method of claim 9 wherein said segment deleted from said second plasmid comprises at least that portion of said ctxA gene sequence which codes for amino acid residues 10 through 164.

12. The method of claim 9 wherein said segment deleted from second plasmid comprises at least 80% of the sequence required for expression of said $A_1$ peptide.

13. A nontoxinogenic genetically stable strain of *Vibrio cholerae* Ogawa 395 derived from a parent *V. cholerae* Ogawa 395 organism comprising at least two copies of the ctxA gene, a ctxB gene, and genes enabling colonization in the human intestine, said strain being derived by genetically engineering a deletion mutation in both said copies of said parent organism ctxA genes resulting in the loss of a gene sequence from each of said ctxA genes required for expression of a toxic $A_1$ peptide;

said strain comprising said ctxB gene and said parent genes enabling colonization in the human intestine.

* * * * *

UNITED STATES PATENT AND TRADEMARK OFFICE
CERTIFICATE OF CORRECTION

PATENT NO. : 4,882,278

DATED : November 21, 1989

INVENTOR(S) : John J. Mekalanos

It is certified that error appears in the above-identified patent and that said Letters Patent is hereby corrected as shown below:

Col. 5　　　　　　　　DNA sequence is incorrect. In the second line, delete the second "ASP" moving the entire line sequence to the left. After "TYR" (in the same line) insert --GLY-- thus returning the line sequence to the right.

Col. 7, line 42　　　delete ";" after "0395-N1".

Col. 9, line 34　　　"5EWD299" should be --EWD299--. and not a new paragraph but rather part of the sentence on the previous line.

Col. 10, line 1　　　"0395-Nt" should be --0395-NT--.

Signed and Sealed this

Twenty-fifth Day of December, 1990

Attest:

HARRY F. MANBECK, JR.

*Attesting Officer*　　　　　*Commissioner of Patents and Trademarks*

UNITED STATES PATENT AND TRADEMARK OFFICE
CERTIFICATE OF CORRECTION

PATENT NO. : 4,882,278

DATED : November 21, 1989

INVENTOR(S) : John J. Mekalanos

It is certified that error appears in the above-identified patent and that said Letters Patent is hereby corrected as shown below:

On the title page:

At column 1, line 5, immediately below the heading "BACKGROUND OF THE INVENTION", please add the following sentence as a separate paragraph:

--This invention was made at least in part with funding from the U.S. Government, (NIH Grant AI18045), and the Government has certain rights in the invention.--

Signed and Sealed this

Second Day of July, 1991

Attest:

HARRY F. MANBECK, JR.

*Attesting Officer*  *Commissioner of Patents and Trademarks*